(12) United States Patent
Gadhe

(10) Patent No.: US 9,670,123 B2
(45) Date of Patent: Jun. 6, 2017

(54) PROCESS FOR PREPARATION OF UNSATURATED KETONE

(71) Applicant: Godavari Biorefineries Limited, Mumbai, Maharashtra (IN)

(72) Inventor: Ravindra Gadhe, Mumbai (IN)

(73) Assignee: GODAVARI BIOREFINERIES LIMITED, Mumbai, Mharashtra (IN)

( * ) Notice: Subject to any disclaimer, the term of this patent is extended or adjusted under 35 U.S.C. 154(b) by 0 days.

(21) Appl. No.: 14/915,052

(22) PCT Filed: Aug. 21, 2014

(86) PCT No.: PCT/IN2014/000538
§ 371 (c)(1),
(2) Date: Feb. 26, 2016

(87) PCT Pub. No.: WO2015/029059
PCT Pub. Date: Mar. 5, 2015

(65) Prior Publication Data
US 2016/0207861 A1    Jul. 21, 2016

(30) Foreign Application Priority Data
Aug. 30, 2013 (IN) .................. 2838/MUM/2013

(51) Int. Cl.
*C07C 45/74* (2006.01)
*C07C 45/82* (2006.01)

(52) U.S. Cl.
CPC ............. *C07C 45/74* (2013.01); *C07C 45/82* (2013.01)

(58) Field of Classification Search
CPC ................................ C07C 45/74; C07C 45/82
USPC ........................................................ 568/390
See application file for complete search history.

(56) References Cited

U.S. PATENT DOCUMENTS

| 3,077,500 A | * | 2/1963 | Heinz | ....................... B01J 31/08 521/32 |
| 5,583,263 A | * | 12/1996 | Muthusamy | ............ C07C 45/62 568/396 |
| 6,977,314 B2 | * | 12/2005 | Vandersall | ............... B01J 31/10 568/388 |

FOREIGN PATENT DOCUMENTS

EP    1000922 B    9/2002

* cited by examiner

*Primary Examiner* — Sikarl Witherspoon
(74) *Attorney, Agent, or Firm* — Haug Partners LLP

(57) ABSTRACT

The present invention relates to a process for preparing unsaturated ketone by using an ion exchange polymer as a catalyst. The process comprises the steps of mixing an aldehyde with a ketone and passing the mixture of aldehyde and ketone through a fixed bed catalytic reactor comprising the ion exchange polymer at a temperature of at least 60 degree C. at atmospheric pressure for a retention period of 30-50 min. The unsaturated ketone obtained from the reaction is purified by distillation and 99.5% pure unsaturated ketone with a yield of not less than 80% is obtained.

12 Claims, No Drawings

PROCESS FOR PREPARATION OF UNSATURATED KETONE

CROSS-REFERENCE TO RELATED APPLICATIONS

This application is the National Stage entry under 35 U.S.C. §371 of International Application No. PCT/IN2014/000538 filed on Aug. 21, 2014, published on Mar. 5, 2015 under publication number WO 2015/029059 A2, which claims the benefit of priority under 35 U.S.C. §119 of Indian Patent Application Number 2838/MUM/2013 filed Aug. 30, 2013.

FIELD OF THE INVENTION

The invention relates to a process for preparation of an unsaturated ketone compound.

BACKGROUND OF THE INVENTION

Unsaturated ketones have numerous applications in organic chemistry. They are generally used as additives during the manufacture of perfumes. Various methods are available in the art for the preparation of unsaturated ketones.

Generally, unsaturated ketones are prepared by aldol condensation of aldehydes with ketone using sulfuric acid as a catalyst. However, this process produces huge amount of toxic wastes so that large amount of effluent treatment is required which results in increase in cost of manufacturing. Also, the yield of the final product the unsaturated ketone is less.

EP1000922B1—Provides for a process of preparing unsaturated ketones by reacting the corresponding α,β-unsaturated alcohols with alkyl acetoacetates in the presence of from 0.1 to 5 mol %, based on the alkyl acetoacetate to be reacted, with an organic aluminum compound as catalyst with elimination and continuous removal by distillation of the carbon dioxide which forms during the reaction and of the alcohol which is eliminated from the acetoacetate in a reactor system with fitted fractionating column, wherein the α,β-unsaturated alcohol is introduced with less than 10% by weight of an inert solvent and with less than 0.5% by weight of a liquid which has a boiling point between that of the alkyl acetoacetate and that of the alcohol to be eliminated there from into the reaction vessel together with the organic aluminum compound, and the alkyl acetoacetate is metered into this mixture, a reaction temperature which is as constant as possible at between 175° C. and 220° C. is adjusted and during the reaction the content of alkyl acetoacetate in the reaction mixture is adjusted to a value which is as constant as possible at between 0.1 and 10% by weight.

The above process is very cumbersome and involves too many steps and the reaction is carried out at a high temperature.

Hence there is a need for a process for preparation of the unsaturated ketone that solves at least one of the problems as defined above and other problems related to the preparation of the unsaturated ketone.

SUMMARY OF THE INVENTION

The present invention relates to a process for preparing unsaturated ketone compound using an ion exchange polymer as a catalyst. The process comprises the steps of mixing an aldehyde with ketone and passing the mixture of aldehyde and ketone through a fixed bed catalytic reactor comprising of the ion exchange polymer at a temperature of at least 60 degree C. at atmospheric pressure for a retention period of at least 30 min. The unsaturated ketone obtained from the reaction is purified by distillation.

DETAILED DESCRIPTION OF THE INVENTION

The present invention provides a process for preparing unsaturated ketone using a catalyst. The process comprises the steps of mixing an aldehyde with ketone and passing the mixture of aldehyde and ketone through a fixed bed catalytic reactor comprising ion exchange polymer at a temperature of at least 60 degree C. at atmospheric pressure for a retention period of at least 30 min. The unsaturated ketone obtained from the reaction is purified by distillation.

The yield of the product is not less than 80% based on Ketone and not less than 75% based on aldehyde.

The unsaturated ketone thus obtained is 99.5% pure.

According to an embodiment of the present invention, the temperature is maintained above the room temperature. According to the preferred embodiment of the invention, the range of the temperature is 60-90 degree C., preferably 70-80 degree C. and more preferably 75-78 degree C.

According to an embodiment of the present invention, the reaction is preferably carried out at atmospheric pressure.

According to an embodiment of the present invention, the predetermined retention period is about 30-50 min, preferably 40 min.

According to the present invention, the selectivity of the catalyst is about 80 mole % based on ketone—or is about 75 mole % based on aldehyde.

According to the present invention, the process further comprises the step of recovery of the unreacted aldehyde and ketone before purification of the unsaturated ketone obtained. The recovery step includes distillation of the reaction mixture of unreacted aldehyde, ketone and unsaturated ketone. The unreacted aldehyde and ketone are dried and recycled back to the reaction mixture.

According to the present invention, the process is continuous process. Alternatively, the process can be a batch or semi continuous process.

According to the present invention the aldehyde is selected from acetaldehyde or butyraldehyde.

According to the present invention the ketone is selected from methyl ethyl ketone or acetone.

According to the present invention, the catalyst is an ion exchange polymer.

According to the preferred embodiment of the present invention, the ion exchange polymer is polystyrene sulphonated or carbonated cation resin wherein the resin is sulphonated or carbonated by sulphonic acid or carboxylic acid. More preferably, the ion exchange catalyst is polystyrene sulphonated cation resin.

A preferred embodiment of the present invention relates to a process for preparation of 3-methyl-3-penten-2-one by using a polymer catalyst. The process comprises the steps of mixing acetaldehyde with methyl ethyl ketone and passing the solution of acetaldehyde and methyl ethyl ketone through a fixed bed catalytic reactor comprising of polystyrene sulphonated cation resin at an atmospheric pressure and at a temperature in the range of 60-90 degrees C. for 30-50 minutes to obtain 3-methyl-3-penten-2-one. The process is carried out in a continuous mode. The crude 3-methyl-3-penten-2-one thus obtained is purified by distillation and 99.5% pure 3-methyl-3-penten-2-one is obtained.

After the reaction is complete, unreacted acetaldehyde and methyl ethyl ketone are recovered by distillation and the recovered acetaldehyde and methyl ethyl ketone are dried and recycled back to the reaction. The yield of 3-methyl-3-penten-2-one is 80%.

The above process can be explained more clearly with the help of the following example but does not limit the scope of the invention to the said example

EXAMPLE 1

400 gms of Acetaldehyde and 3200 gms of Methyl ethyl ketone were mixed and passed into the reaction column and the reactants were then passed through a fixed bed catalyst column consisting of 300 ml of polysterene sulphonated cation resin at atmospheric pressure and at the rate of 6 gm/min at 76 Deg C. The conversion of acetaldehyde was 80% and methyl ethyl ketone was 16 mole %. The unreacted acetaldehyde and methyl ethyl ketone were recovered by distillation. The recovered acetaldehyde and methyl ethyl ketone were dried and recycled into the reaction. The crude product thus obtained was 3-methyl-3-penten-2-one which was further purified by distillation and obtained 475 gms of 99.5% pure 3-methyl-3-penten-2-one was obtained and the yield was 80%.

EXAMPLE 2

133 gms of Acetaldehyde and 3200 gms of Methyl ethyl ketone solution were mixed and passed through a three numbers of column which is in series with fixed bed catalyst consisting of 300 ml of polysterene sulphonated cation resin of each column at an atmospheric pressure of 18 gm/min at 75 deg C. The outlet from each column added 133 gms of fresh acetaldehyde instead of mixed total quantity of acetaldehyde initially with methyl ethyl ketone. The conversion of acetaldehyde was 85% and methyl ethyl ketone was 16 mole % per pass. The unreacted acetaldehyde and methyl ethyl ketone were recovered by distillation. The recovered acetaldehyde and methyl ethyl ketone were dried and recycled into the reaction. The crude product thus obtained was 3-methyl-3-penten-2-one which was further purified by distillation and obtained around 520 gms of 99.5% pure 3-methyl-3-penten-2-one and the yield was 70%.

EXAMPLE 3

400 gms of Butyraldehyde and 1000 gms of Acetone were mixed before passing into the reaction column and the reactants were then passed through a fixed bed catalyst column consisting of 300 ml of polysterene sulphonated cation resin at atmospheric pressure and at the rate of 6 gm/min at 65 deg C. The conversion of butyraldehyde was 50 mole % and Acetone was 10 mole %. The unreacted butyraldehyde and acetone were recovered by distillation. The recovered butyraldehyde and acetone were dried and recycled. The crude product thus obtained was 4-butyl-3-heptene-2-one which was further purified by distillation and obtained around 217 gms of 99.5% pure 4-butyl-3-heptene-2-one was obtained and yield was 70%.

The foregoing description of the invention has been set merely to illustrate the invention and is not intended to be limiting. Since modifications of the disclosed embodiments incorporating the spirit and substance of the invention may occur to person skilled in the art, the invention should be construed to include everything within the scope of the disclosure.

The invention claimed is:

1. A process for selectively preparing an unsaturated ketone which is obtained from a reaction of an aldehyde with a ketone followed by dehydration in the same reaction mixture, the process comprising the steps of—
    mixing an aldehyde with a ketone;
    passing the mixture of aldehyde and ketone through a fixed bed catalytic reactor comprising polystyrene sulphonated cation resin or polystyrene carbonated cation resin;
    at a temperature of 60-90 degrees C.;
    at atmospheric pressure for a retention period of 30-50 minutes;
    to obtain said unsaturated ketone in a yield of at least 70% and a purity of about 99.5%.

2. The process for preparing an unsaturated ketone as claimed in claim 1, wherein the range of the temperature is 70-80 degree C.

3. The process for preparing an unsaturated ketone as claimed in claim 1, wherein the aldehyde is selected from acetaldehyde or butyraldehyde.

4. The process for preparing an unsaturated ketone as claimed in claim 1, wherein the ketone is selected from methyl ethyl ketone or acetone.

5. The process for preparing an unsaturated ketone as claimed in claim 1, wherein the ion exchange polymer is polystyrene sulphonated cation resin.

6. The process for preparing an unsaturated ketone as claimed in claim 1, wherein the retention period is about 40 min.

7. The process for preparing an unsaturated ketone as claimed in claim 1, wherein the selectivity of the catalyst is 80 mole % based on the ketone or is 75 mole % based on the aldehyde.

8. The process for preparing an unsaturated ketone as claimed in claim 1, wherein the process further comprises the step of recovering, drying and recycling of the unreacted aldehyde and ketone, the recovery step includes distillation of the reaction mixture of unreacted aldehyde, ketone and the unsaturated ketone.

9. The process for preparing an unsaturated ketone compound as claimed in claim 1, wherein, the process is a batch or semi continuous or continuous process.

10. A process for preparing 3-methyl-3-penten-2-one, the process comprising:
    mixing acetaldehyde with methyl ethyl ketone;
    passing the solution of acetaldehyde and methyl ethyl ketone through a fixed bed catalytic reactor comprising polystyrene sulphonated cation resin at atmospheric pressure and at a temperature in the range of 60-90 degrees C. for 30-50 minutes in continuous mode; to obtain said 3-methyl-3-penten-2-one in a yield of at least 70% and a purity of about 99.5%.

11. A process for preparing 3-methyl-3-penten-2-one as claimed in claim 10, wherein the temperature is 75-78 degree C. and the retention period is 40 min.

12. The process for preparing 3-methyl-3-penten-2-one as claimed in claim 10, wherein the acetaldehyde and methyl ethyl ketone are further recovered, dried and recycled.

* * * * *